United States Patent [19]

Lagarde et al.

[11] Patent Number: 5,403,825
[45] Date of Patent: Apr. 4, 1995

[54] METHOD FOR ISOLATING A SOLUBLE OSTEOGENIC FACTOR FROM BONE

[75] Inventors: Alain E. Lagarde, Kingston; Abdulwahid Abdulwajid, Toronto; Donna Bueschkens, Mississauga; Deanna Byrne, Scarborough, all of Canada

[73] Assignee: Allelix Biopharmaceuticals Inc., Mississauga, Canada

[21] Appl. No.: 937,744

[22] Filed: Sep. 1, 1992

Related U.S. Application Data

[62] Division of Ser. No. 676,179, Mar. 28, 1991, Pat. No. 5,169,837.

[51] Int. Cl.$^6$ ............... C07K 15/06; A61K 37/02
[52] U.S. Cl. ............... 514/21; 530/412; 514/2
[58] Field of Search ............... 530/412; 514/2, 21

[56] References Cited

U.S. PATENT DOCUMENTS

| | | | |
|---|---|---|---|
| 3,458,397 | 7/1969 | Myers | 195/2 |
| 4,444,760 | 4/1984 | Thomas, Jr. | 514/121 |
| 4,563,350 | 1/1986 | Nathan | 424/95 |
| 4,627,982 | 12/1986 | Seyedin | 424/95 |
| 5,169,837 | 12/1992 | Lagarde | 514/21 |

OTHER PUBLICATIONS

Tornberg, et al., "Activation of the Resting Periosteum", Clinical Orthopaedics and Related Research, vol. 129, Nov.-Dec. 1977, pp. 305-312.
Clark, et al., "Bone-Cell-Stimulating Substance", Clinical Orthopaedics and Related Research, vol. 237, Dec. 1988, pp. 226-235.

*Primary Examiner*—Robert J. Hill, Jr.
*Assistant Examiner*—Carol Salata
*Attorney, Agent, or Firm*—Foley & Lardner

[57] ABSTRACT

Described is a purified osteogenic factor that when delivered to bone in association with a physiologically acceptable delivery vehicle is capable of inducing new bone growth at the bone surface. The osteogenic factor is water soluble, and is characterized physically by a molecular weight of about 2.5 kD when measured by gel filtration under dissociating conditions and an isoelectric point in the pH range from about 4.6 to 7.2. Use of the purified factor in treating bone defects is described. Also described is a method for obtaining the purified factor from mammalian bone.

5 Claims, 10 Drawing Sheets

C8 REVERSE-PHASE HPLC

METHOD FOR ISOLATING A SOLUBLE OSTEOGENIC FACTOR FROM BONE

This application is a division of application Ser. No. 07/676,179, filed Mar. 28, 1991, now U.S. Pat. No. 5,169,837.

FIELD OF THE INVENTION

This invention relates to compounds and compositions useful therapeutically to heal and repair mammalian bone. More particularly, the invention relates to a novel osteogenic factor that is recoverable from mammalian bone extracts and useful to induce bone formation.

BACKGROUND OF THE INVENTION

Bone is a mineralized tissue of complex chemical and cellular composition which is continuously remodelled throughout the mammalian life span. Underlying the remodelling process are cells of the osteoblast lineage which participate in bone formation, and cells of the osteoclast lineage which participate in bone resorption. These two types of cells are known to originate from distinct early progenitor cells, i.e. stem cells, which differentiate along separate pathways into mature and functional cells, in response to such endogenous mediators as systemic hormones, cytokines and growth factors.

Some of the molecules that are presumed to control biological processes essential to bone development and repair have been isolated and biochemically identified, and recombinant DNA technologies have been applied to produce relatively large quantities of those having a protein-based structure. These advances are expected ultimately to provide physicians and surgeons with defined therapeutic compositions that can be administered in clinical situations when accelerated healing, sustained repair or reconstruction of skeletal and cranio-maxillofacial defects are desired, e.g. union of fractures caused by trauma or as a consequence of osteoporosis, autogenous and allogenic bone grafts, plastic surgery, and correction of congenital deformities.

Many of the compounds having a beneficial effect on bone development are proteins and glycoproteins that can be identified in or were isolated originally from extracts of demineralized i.e. acid-treated mammalian bone. These may be categorized into three distinct classes.

One class of molecules having an effect on bone cell activity includes mitogenic substances which for the most part were known previously to have a mitogenic effect on cells types other than bone cells, such as fibroblasts. Among the molecules in this class are polypeptides that exhibit heparin-binding affinity, such as acidic fibroblast growth factor (15–18 kDa) and basic fibroblast growth factor (18–22 kDa) as well as platelet-derived growth factor (28–31 kDa) and a high molecular weight (83 kDa) isoform of insulin-like growth factor II originally called skeletal growth factor.

A second class of osteogenic molecules includes cartilage-inducing factors, designated CIF-A (26 kDa) and CIF-B (26 kDa) which are identical with transforming growth factors TGF-B1 and TGF-B2. It has been demonstrated that TGF-B2 is effective in promoting bone mass increases in several animal models, but only after repeated (daily) injections of doses in excess of 250 ng. Daily injection is also required to attain increased bone mass when the osteogenic factor (1.5 kDa, pI>11) disclosed in Canadian patent application 2,010,660 is employed.

A third class of osteogenic molecules includes several related members of a family of glycosylated proteins characterized by: a dimeric structure; a molecular weight in the 25 to 30 kDa range; the presence of several interchain disulfide bonds essential to bioactivity; moderate affinity for heparin; substantial amino acid homology with species of TGF-B; and the ability to initiate bone formation at non-bone sites when combined with a bone-compatible matrix and administered to rats. Included in this class are the several species of "bone morphogenetic protein" (28–30 kDa). Also included are substances that are less well characterized but share at least one characteristic with members in this class, such as the osteogenic factor (22–24 kDa) disclosed in U.S. Pat. No. 4,804,744.

As mentioned above, these osteogenic substances have for the most part been detected in, and isolated from, extracts of previously demineralized mammalian bone fragments. In the extraction protocol commonly applied to the demineralized material, use is made of extractive solutions that include a dissociating agent such as urea or guanidinium hydrochloride, to assist in separation of macromolecular aggregates, and include a combination of inhibitors of proteolytic activity to reduce digestion of the protein component released during extraction. An alternative approach to generating mammalian bone extracts as described in U.S. Pat. No. 3,458,397, in which fragmented bone is exposed to both a strong demineralizing acid and to the protein-digesting agent pepsin, has lead to the isolation of osteogenic material that induces remarkable increases in bone growth.

According to U.S. Pat. No. 3,458,397, osteogenic material is provided when acid/pepsin-treated calf bone extracts are precipitated in ethanol and then stripped with water to yield the insoluble component. As reported by Tornberg et al in Clinical Orthopaedics and Related Research, 1977, 129:305–312 and later in the same journal by Clark et al, 1988, 237:226–235, this osteogenic material results in a dramatic increase in bone weight when administered, in a phosphate-buffered saline vehicle, at the bone surface. A single injection of a 6 mg dose of the osteogenic material was found to induce an increase in the dry weight of rat limb bone of up to 30% relative to the untreated contralateral limb, with the maximum effect being realized at about 7 days after injection.

Though the effect on bone growth induced by the osteogenic material is a desirable one, and is valuable particularly in the context of fracture repair, the crude state of the material makes it inappropriate for use as a human therapeutic.

It is an object of the present invention to provide an isolated osteogenic factor.

It is another object of the present invention to provide an osteogenic composition useful to induce bone growth.

It is another object of the present invention to provide a method for inducing bone formation in a mammal.

SUMMARY OF THE INVENTION

There has now been isolated from crude extracts of mammalian bone a novel osteogenic factor capable of inducing bone growth when delivered to bone in association with a physiologically acceptable delivery vehicle. More particularly and in accordance with one aspect of the present invention, there is provided an isolated, water-soluble osteogenic factor characterized by a relatively low molecular weight of about 2.5 kDa as measured by filtration on Sephacryl S300 under dissociating conditions, a mildly acidic isoelectric point in the pH range from about 4.6 to 7.2, and a specific activity of at least about 10 units/mg of protein, as determined in the rat bone growth assay. The present invention also provides the osteogenic factor in purified form, characterized by migration as an individualized peak at 214 nm on reversed-phase high performance liquid chromatography and a specific activity of at least about 3,000 units/mg.

According to another aspect of the present invention, there is provided an osteogenic composition comprising an effective amount of the osteogenic factor of the present invention, in combination with a physiologically acceptable delivery vehicle. There is further provided, in a related aspect of the present invention, a method for preparing an osteogenic composition, comprising the step of combining a physiologically acceptable delivery vehicle with an amount of the osteogenic factor effective to induce bone formation.

According to another aspect of the present invention, there is provided a method for inducing bone formation in a mammal, which comprises the step of delivering an osteogenic composition of the invention to bone at the site at which bone formation is desired.

In a further aspect of the present invention, there are provided methods for isolating and purifying the present osteogenic factor from mammalian bone extracts, as hereinafter described.

BRIEF DESCRIPTION OF THE DRAWINGS

The present invention and its preferred embodiments are now described with reference to the accompanying drawings in which.

DETAILED DESCRIPTION OF THE INVENTION AND ITS PREFERRED EMBODIMENTS

The invention relates to a water-soluble, osteogenic factor that induces bone formation in mammals when delivered to a bone surface in association with a physiologically acceptable delivery vehicle.

As distinct from other osteogenic factors, the present osteogenic factor is characterized in terms of its physical properties by the combination of relatively low molecular weight of about 2.5 kDa as measured by gel filtration under dissociating conditions, and by an isoelectric point in the pH range from about 4.6 to about 7.2. As judged by its behaviour when subjected to various techniques of separation, the isolated osteogenic factor appears also to be polypeptide in nature, and to possess substantially no heparin-binding affinity. Further, the factor retains bone formation-inducing activity following exposure to reducing agents, suggesting that the integrity of disulfide bonds, if present, are not required for activity. Also, assays have revealed that the factor does not act in vitro as a mitogen on either osteoblasts or fibroblasts.

The present osteogenic factor is a component of mammalian bone and can be recovered therefrom in isolated and purified form by applying conventional separation techniques in a combination selected to exploit the characterizing physical and biological properties of the factor. Desirably, the osteogenic factor is isolated from an extract of mammalian bone that has first been digested to liberate its endogenous components. Bone digestion can be achieved by subjecting washed and crushed bone to demineralization, for example by exposure to aqueous acid e.g. HCl. For the purpose of extracting the present osteogenic factor, bone digestion can proceed in the absence of protease inhibitors used conventionally in the art. More suitably, digestion is achieved using a combination of demineralizing acid and a protein-digesting agent such as pepsin. Following bone digestion, the osteogenic factor is present in the soluble phase and can be precipitated therefrom with an alkanol such as ethanol. Following exposure to ethanol, the osteogenic factor resides in the insoluble phase, which serves as a useful source for isolation of the present osteogenic factor.

A specific protocol useful for generating the ethanol-precipitated bone extract containing the osteogenic factor is described by Myers et al in U.S. Pat. No. 3,458,397, the contents of which are incorporated herein by reference. This protocol exploits cancellous calf bone as an extract source, although it will be appreciated that bones obtained from other mammals, such as horse, pig, and humans may also yield an extract containing the present osteogenic factor or homologue thereof when subjected to such an extraction protocol.

The osteogenic factor is a water-soluble component of the ethanol-precipitated bone extract. Accordingly, it is desirable to strip the extract of osteogenic factor by washing with water, preferably with at least two cycles of water washing. In this regard, it is desirable to disregard the guidance provided by Myers et al supra, and to retain the washings rather than the insoluble residue that remains after water-stripping of the ethanol precipitate. The water-insoluble residue is substantially devoid of osteogenic activity when subjected to three or more cycles of washing, and can be discarded. The remaining aqueous extract, also referred to herein as enriched bone extract, represents a useful source of osteogenic factor, and can be stored in lyophilized form if desired.

Once the aqueous extract is obtained, the osteogenic factor therein can be isolated by separating the factor from other resident components by subjecting the extract to selected separation techniques. Dissociating conditions should be employed during isolation, in order to prevent formation within the aqueous extract of macromolecular aggregates. Dissociating agents such as urea and guanidinium chloride are suitable for this purpose. Separation on molecular sieves is useful, for example, to exclude higher molecular weight extract components from those having a molecular weight similar to that of the osteogenic factor. When fractionation by gel filtration is employed, for instance, those fractions that under dissociating conditions elute with an apparent molecular weight of less than about 8 kDa can be collected, to eliminate higher molecular weight contaminants. Affinity chromatography is also useful for separating components in the extract. In particular, the osteogenic factor has substantially no affinity for heparin, and the extract can thus be fractionated on a heparin-binding column e.g. heparin-sepharose, in order to eliminate heparin-binding components retained on the column. Also, the osteogenic factor displays some affinity for hydroxyapatite and hydroxyapatite affinity columns may also be used to fractionate the extract sources of the factor. Ion exchange columns, including columns that bind anionic species such as diethylaminoethyl (DEAE) or cationic species such as carboxymethylcellulose (CMC), are also useful for isolating the osteogenic factor, and elution conditions can be selected having regard for the isoelectric point of the factor, which is in the range from about pH 4.6 to about pH 7.2. Also particularly useful, desirably as the last phase in the isolation procedure, is reversed-phase high performance liquid chromatography (HPLC).

The particular sequence in which selected separation techniques are applied to fractionate the extract and isolate the osteogenic factor can vary, but generally are combined in the manner most efficient for recovery of the factor in substantially purified form. According to one embodiment of the invention, a three step isolation protocol is employed which yields the osteogenic factor in a homogeneous form, characterized by migration as a prominent and well individualized absorbance peak at 214 nm on reversed phase HPLC. In this three-step protocol, aqueous extract of the ethanol-precipitate obtained as described above is lyophilized and resuspended in buffer containing a dissociating amount of urea and then applied to a gel filtration column e.g. Sephacryl S300. Fractions eluting with an estimated molecular weight of less than about 8 kDa are pooled and then applied to an anion exchange column e.g. DEAE-Cellulose, and fractions eluting in concentrations of sodium chloride at and above about 200 mM are then collected. Fractions collected from the anion exchange column are then pooled and subjected to reversed phase HPLC, such as on a C-8 reversed phase column. The osteogenic factor elutes at between 15% and 20% acetonitrile as a well individualized absorbance peak at 214 nm. Material which when loaded onto the reversed phase column migrates as a single peak can be obtained by re-chromatographing if desired. A specific protocol for performing this three step isolation procedure is detailed in example 2 herein.

The three-step protocol just described can of course be modified. For example, the first size exclusion step is dispensible, and the water-extracted osteogenic material can be subjected directly to ion exchange chromatography, using conditions exemplified herein in order to collect bioactive fractions, that may then be pooled and subjected to reversed phase HPLC. Alternatively, the ion exchange step may be performed on a carboxymethyl cellulose column at an acidic pH, rather than on the DEAE column, if desired.

The bone formation-inducing activity of the osteogenic factor can be monitored during the isolation procedure using an activity assay herein referred to as the "rat bone growth assay". This assay compares the increase in dry weight of rat bone treated with osteogenic factor, relative to an untreated contralateral bone control. The assay is performed in the manner detailed in the examples hereto. Briefly, injectable solutions containing the osteogenic factor are prepared by combining a factor-containing preparation with a hydroxyapatite matrix and an aqueous buffered solution and then delivered to the limb of a rat by single injection alongside i.e near the surface of, the tibia-fibula complex. A control dose, devoid of osteogenic factor, is similarly delivered to the contralateral limb. The treated and untreated bones are removed about 7 days after treatment, the bones are freed of soft tissue, washed and then dried. The increase in bone mass induced by the osteogenic factor preparation is then measured as the difference in dry weight between the treated and control bones. Depending on the amount of osteogenic factor contained in the injected preparation, a bone weight increase in excess of 25% can be observed. The effect induced by the factor is manifest principally as a visible increase in bone girth as opposed to increased bone length.

A unit (U) of osteogenic activity is hereindefined as the amount of osteogenic factor preparation (measured as milligrams of protein) required to induce half-maximum bone mass increase after 7 days, under the conditions of the bioassay specified above. Typically, the water soluble protein extract i.e. the enriched bone extract starting material, exhibits an activity of about 1 unit/mg prior to purification.

The effect on bone growth of preparations recovered at various stages during osteogenic factor isolation is revealed by specific activities determined after establishing dose-response curves. As is revealed by the dose-response curves presented in FIG. 9, fractionation of the enriched bone extract by gel filtration has the effect of increasing specific activity to about 10 units/mg of protein. Subsequent fractionation on DEAE-cellulose columns provides a further increase in specific activity, to about 600 units/mg. Material migrating as an individualized peak following passage through a reversed phase HPLC column, herein referred to as "purified" osteogenic factor, possesses a specific activity of at least about 3,000 units/mg, maximally to about 4,000 units/mg.

According to one embodiment of the invention, the purified osteogenic factor is converted to a powdered form by lyophilization, in order to facilitate formulation thereof, to enhance storage stability and to eliminate contaminating solvent.

To exploit therapeutically the bone formation-inducing properties of the osteogenic factor, osteogenic compositions are prepared by combining a therapeutically effective amount i.e a bone formation-inducing amount, of the purified osteogenic factor with a physiologically acceptable vehicle. Delivery vehicles suitable for use with the osteogenic factor can be of a type conventionally employed in delivering to bone surfaces other bone therapeutic agents, such as the various species of bone morphogenetic protein. Most preferably, the delivery vehicle includes as one component a bone-compatible matrix material which serves to mediate the bone-forming activity of the osteogenic factor at the bone surface. As used herein, the term "bone-compatible" refers to substances having no substantially adverse effect e.g. toxic effect, on bone or surrounding tissue while resident at the bone surface. Suitable for use as a matrix material are those substances, or combinations thereof, that when combined with the purified osteogenic factor generate a positive result in the rat bone growth assay herein described. Such matrix materials include bone-derived materials, such as osteogenically "deactivated" bone extract that results following separation from the osteogenic factor. More preferably, the bone-compatible matrix consists of chemically defined material, to allow for greater control during dosage formulation. In this regard, suitable matrix materials include bone-produced substances having no bone formation-inducing activity per se, such as hydroxyapatite, and collagen. Also useful as matrix materials are calcium sulphate, tricalcium phosphate, polylactic acids including polylactide, polyglycollic acid, polyglactin and polyglactic acid, polyanhydrides, polymethylmethacrylate and gelatin. Such materials can be used alone or in any useful combination. For example, it has been found that hydroxyapatite per se is useful as a matrix material, but is useful also in combination with collagen and gelatin.

In addition to bone-compatible matrix material, the physiologically acceptable delivery vehicle may contain a pharmaceutically acceptable carrier or diluent. The use of such carriers and diluents is desirable particularly to prepare formulations suitable for transdermal delivery e.g. by injection. For example, injectable formulations of the osteogenic composition can be prepared, for subcutaneous delivery, by mixing an effective amount of the purified osteogenic factor with a delivery vehicle consisting of a physiologically buffered saline solution and a selected matrix material, such as hydroxyapatite. Similarly, carriers suitable for formulating viscous compositions, such as cements, pastes and gels, can be employed.

Alternative forms of the osteogenic composition may also be prepared that are suitable for delivering the osteogenic factor by modes other than injection. For example, porous ceramic compositions may be formulated using sintered tricalcium phosphate as matrix material. This provides a slow release, biodegradable form of composition useful to repair bone defects. Reference may be made to U.S. Pat. No. 4,596,574 for guidance on preparing such compositions.

The osteogenic composition will be useful to heal or repair various bone defects such as those arising from disease, from damage induced by trauma or arising congenitally or those induced as a consequence of surgery. The compositions will also be useful in bone grafting. The particular mode of administration will depend on the nature of the bone defect to be treated. In those circumstances when bone to be treated is exposed, for example during bone grafting by surgical intervention, the composition may be layered directly on the surface by application as a cement, gel or paste or may be deposited in the form of an implant.

In one embodiment of the invention, the osteogenic composition is used to promote healing of bone fractures. For this purpose the composition can be in the form of an aqueous buffered solution containing a unit dose of the purified factor in combination with a desired matrix material, such as hydroxyapatite or collagen. The composition is delivered by injection to the site at which the fracture has occurred. For fractures of a medically serious nature, surgical intervention will permit delivery of the composition directly onto the bone surface.

The particular dosage regimen for a given application will ultimately be determined by the attending physician, and will take into consideration such factors as the site and severity of bone damage. Defined dosage ranges can be determined in properly designed clinical trials with patient progress being tracked periodically by x-ray monitoring or if necessary by surgical exploration. Preliminary guidance useful to determine dosage sizes appropriate for human patients can be taken from the results herein presented for the rat bone growth assay. It will be noted, for example, that one-time injection of a sub-microgram quantity of the purified factor caused a significant increase in tibia-fibula weight, from about 100 mgs to about 120 mgs, within about seven days post-injection. This translates roughly to a dose of about 10 ug of purified factor for each gram of bone to be treated, to achieve maximal bone mass increase. Significantly, the increased bone mass is sustained over a period of about one month from single injection, thus it is unlikely that a daily dosage regimen is essential in the bone healing/repair therapy.

It will be appreciated that the osteogenic factor will also have veterinary applications. Particularly, domestic animals and thoroughbred horses in addition to humans are desired patients for such treatment. When used for veterinary purposes, it will be appreciated that the purity of the osteogenic factor can be less of a concern than for human applications. Accordingly, it may be more appropriate to use a preparation having a specific activity of at least about 10 units/mg, up to about 500 units/mg, rather than using the purified material.

EXAMPLES

The protocol described by Myers et al in U.S. Pat. No. 3,458,397 was followed, with minor modification, in order to generate ethanol precipitated bone extract containing the present osteogenic factor. In particular, cancellous calf bones crushed to particles no larger than 1 $mm^3$ were obtained from ANTECH, Animal Technologies (Tyler, Tex.), kept in a Kelvinator freezer at −80° C., and processed within a period of 3 months. They represent the most distal parts (6 cm) of isolated metacarpals and metatarsals. When required, desired amounts of the stored bone fragments (approximately 4 kg per batch), were obtained and allowed to thaw at room temperature (15°–25° C.) in a large beaker. Extraction and solubilization of bone components were then carried out substantially as described by Myers et al U.S. Pat. No. 3,458,397, with minor modifications, up to and including the alcohol precipitation step.

Specifically, the pulverized bones were suspended in 10 litres of an aqueous solution containing 15% NaCl (w/v) and 0.3% toluene (v/v), and stirred at 4° C. for 2 hours. The bone fragments were recovered as a pellet after centrifugation (5,000 rpm×7 min, Sorwall RC-3B), and the pink supernatant was discarded. The same washing operation was repeated once with the 15% NaCl solution (18 hours of contact), then with water (2 hrs of contact). The resulting washed pellet was resuspended into 9 litres of water and transferred into the glass vessel of a 20 litre fermentor (MBR BioReactor AG, Wetzikon, Switzerland). The apparatus is designed to maintain a controlled temperature (set at 37±2° C.) and a steady pH (set at 3.0±0.2). The aqueous bone suspension was stirred at moderate speed (400 rpm) and the pH was adjusted by the automatic addition of concentrated (6N) HCL. One hour later, when the pH was stabilized at 3.0, enough porcine pepsin (crystallized and lyophilized; specific activity=2,345 units per mg of protein, purchased from Sigma Chemical Co., St. Louis, Mo.) was added to the reaction vessel to provide 10 million units of enzymatic activity per kg of bone fragments. After an incubation period of about 48 hours (and generally not less than 24 hours), the suspension was centrifuged (5,000 rpm×20 min) to separate a pellet comprising demineralized bone fragments, which was discarded, from a supernatant which contains soluble minerals and organic bone constituents. This supernatant was collected and refrigerated at 4° C. After decantation an upper layer composed of oily material released during the prior step was carefully aspirated and discarded. To the aqueous solution still having an acidic pH (3.2±0.2) was added 100% pure ethanol (precooled overnight at −20° C.) to bring its final concentration to 30% (v/v). This addition was done slowly over a 10 min period, under moderate stirring. The solution was left undisturbed in a cold room until a white precipitate formed, usually within about 20-24 hours. This first precipitate was collected by centrifugation (5,000 rpm×30 min) and the alcoholic supernatant was saved and left undisturbed in the cold room until the precipitation process was complete, as evidenced by the progressive turbidity of the solution which culminated after about 36 hours. A second precipitate was collected by centrifugation whereas the remaining ethanol supernatant was discarded. Both ethanolic precipitates, which contain the osteogenic factor, were combined, resuspended into 400 ml of water and titrated to pH 7.2±0.3 with 5N NaOH. The neutralized solution was finally subjected to lyophilization after which a powder was obtained.

On average this method yields 40±10 g of alcohol-precipitated powder per kg of pulverized calf bones. The protein content of this dry material, as estimated with the bicinchoninic acid (BCA) dye purchased from Pierce, Rockford, Ill., and using bovine serum albumin as a standard, averaged 13 mg per g of dry weight but was as high as 30 mg for some processed batches.

The lyophilized ethanol precipitates were next treated to enrich for osteogenic activity in the manner described in example 1 below.

Example 1—Isolation of Osteogenic Factor

Ethanol precipitates were resuspended in water at room temperature (15°-25° C.) at 1.5 g/ml with stirring for 20-30 min, and then centrifuged (1,500 rpm×10 min). The supernatant was saved and the pellet was submitted to a second water extraction under the same conditions. The resulting washed pellet which contains less than 0.6 mg of proteins per g of dry weight, and which is devoid of the relevant biological activity, was discarded. The first and second aqueous supernatants were combined and subjected to lyophilization. This lyophilized powder, which will be referred to hereafter as "enriched bone extract", was found to contain the osteogenic factor activity, and was kept in a dessicator at −20° C.

The protein recovery from the dry ethanolic precipitate after the two-step water extraction averages 53% but can be as high as 90%. The successive steps included in the described extraction procedure yield 1.5±0.2 g (dry weight) on average, and a minimum of 150±50 mg (protein) of enriched bone extract respectively per kg of treated calf bone fragments. The solubility of this preparation in aqueous solvents or diluted acids (0.1 N acetic acid) is not complete; the rehydrated enriched bone extract is more accurately characterized as a microparticulate suspension. As revealed below, this suspension was found to have ostegenic activity in the rat bone growth assay.

Bioassay for Testing Osteogenic Potential

Figure 1:
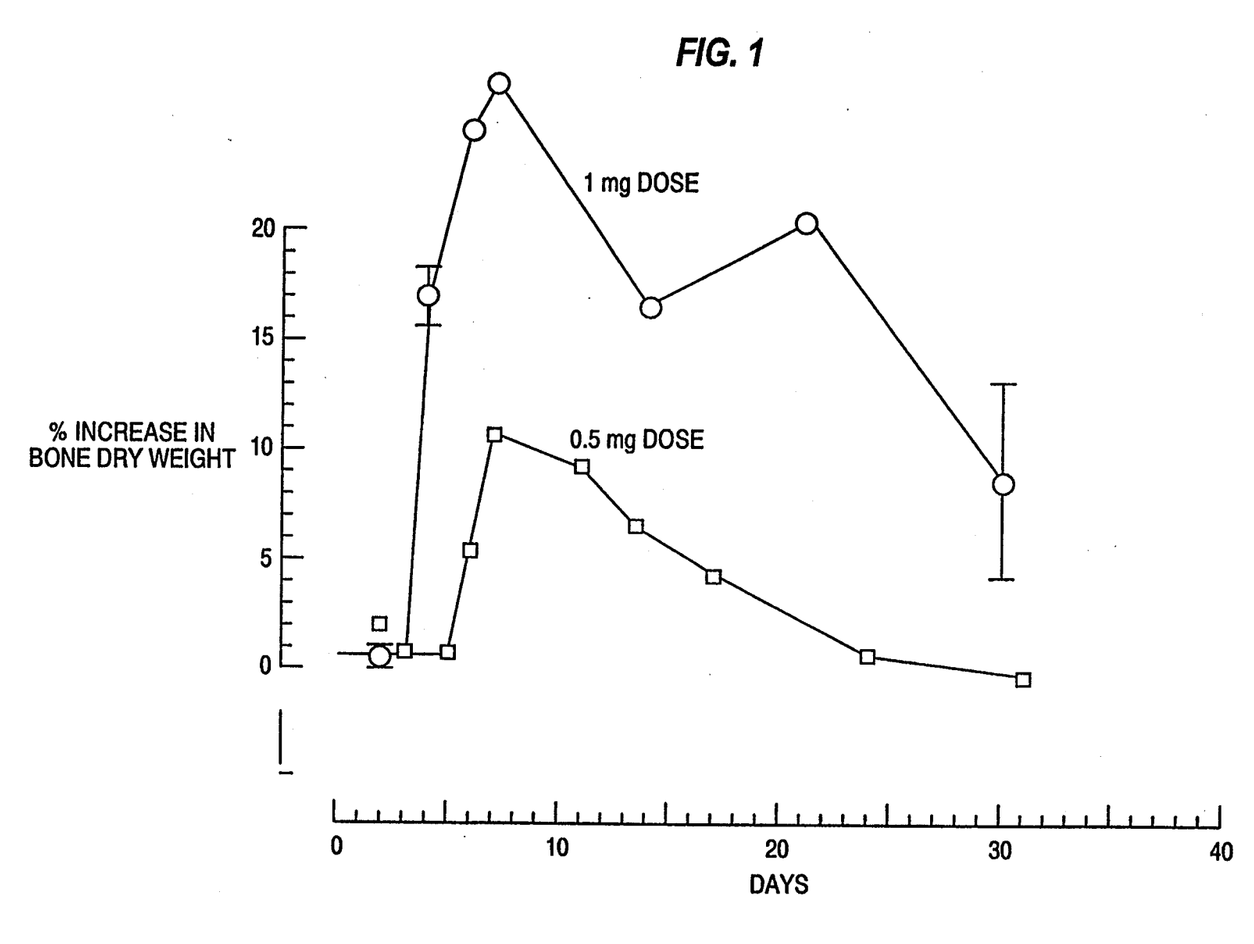
FIG. 1 graphically illustrates the osteogenic response induced when enriched calf bone extract is delivered to a bone surface.

The rat bone growth assay is performed using suspensions prepared by mixing variable amounts of enriched bone extract, ranging between 1 and 20 mg of dry weight, with 1 mL of sterile physiological solution (0.85% NaCl). No more than 0.1 mL of such suspension is injected with a disposable syringe into young Wistar rats (body weight 150±20 g). The preparation is slowly delivered in the vicinity of long bones such as the radius-ulna complex, but preferentially near the knee joint, close to the upper part of the tibia, at the interface between the bone surface and the attached muscle ligaments, without penetrating or damaging the tibia itself. Each animal receives a single dose and at a single site. A control dose, devoid of bone extract, is similarly injected either in the contralateral limb of the same animal, or in a separate recipient. At various periods thereafter, ranging from 4 to 30 days, conveniently after 7 days, the animals are sacrificed and the two tibia-fibula complexes are dissected, isolated and carefully freed from soft tissues. These isolated bones can be kept in a fixative solution composed of formaldehyde (10%) in 100 mM acetate buffer, pH 5.5. The bones are retrieved from the fixative solution, rinsed briefly with water and dried in an oven at 60° C. for 15 to 20 hours. The bone mass increment specifically induced by the inoculum that contained the enriched calf bone extract is measured as the difference in dry weight (in mg) between the tested and control rat tibia-fibula complex, but more precisely as a percentage (%), taking the control bones isolated from the contralateral limb of the same individual as a reference. Typically, the biological response to suspended enriched bone extracts develops after a latency period of 4 to 5 days, peaks at 7-8 days, and decays thereafter at a variable rate which depends on the dose inoculated, as illustrated in FIG. 1. The maximum increase in bone mass, which never exceeds 25±5%, augments as a function of the dose inoculated but is saturable.

Figure 2:
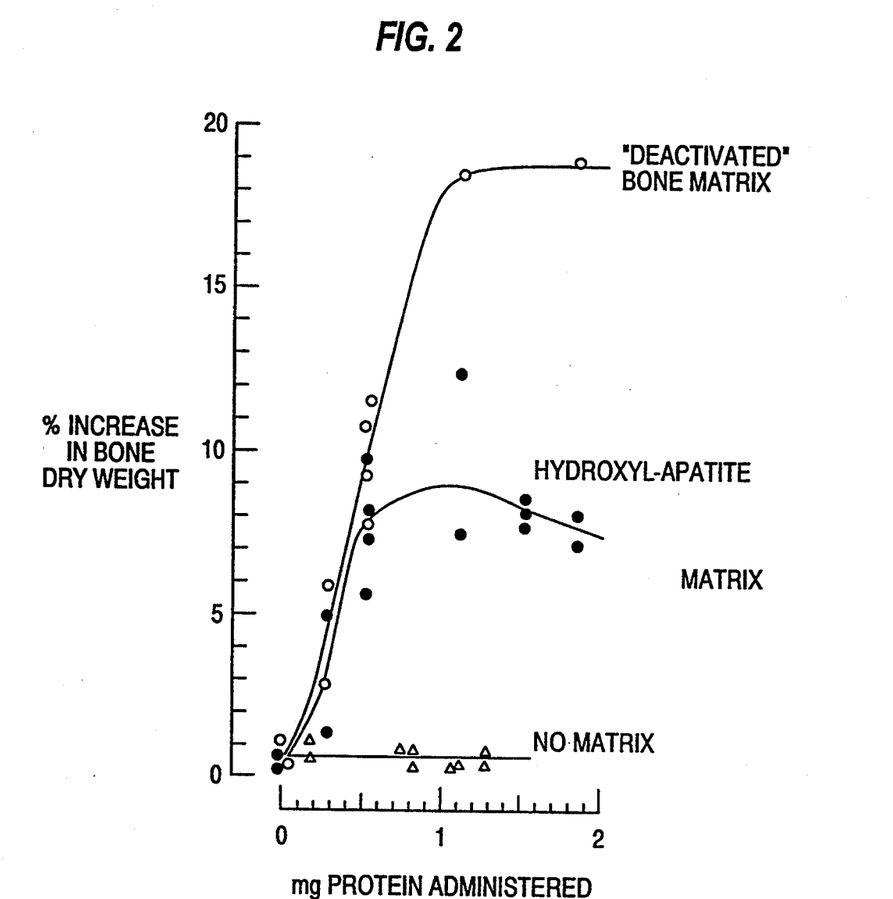
FIG. 2 graphically illustrates the dose-response relationships established when the isolated osteogenic factor is delivered to a bone surface in combination with selected delivery vehicles.

A modified version of the bioassay described above has been used routinely to monitor the enrichment in osteogenic activity during subsequent purification steps, which impose working with solutions rather than with suspensions. A suspension is prepared by mixing an amount of enriched calf bone extract, not exceeding 200 mg of dry weight, with 1 mL of an aqueous solution containing various buffers, salts and other agents as specified below. This suspension is incubated at 37° C. for 15 to 30 min and spun down in a bench top centrifuge (Eppendorf; 12,000 g×5 min). The supernatant is carefully aspirated and its protein content is determined, using the BCA dye method (Pierce) and bovine serum albumin as a standard. Aliqots of the supernatant are mixed with a constant amount (either 0.5 mg or 1 mg dry weight) of Hydroxyl-Apatite (HAP, purchased from Sigma) and are subjected to lyophilization. The resulting dry powder is reconstituted into a volume of physiological saline solution suitable for injection into recipient rats as detailed above. As such, this protocol establishes that the osteogenic potential of re-hydrated enriched bone extracts, exemplified in FIG. 1, resides in an apparently water-soluble protein fraction, since neither the insoluble and protein-depleted residue (also referred to as deactivated bone-derived matrix) that can be separated by centrifugation, nor the artificial and protein-free HAP matrix alone, are bioactive. As illustrated in FIG. 2, the biological response under these conditions obeys a protein dose-dependent relationship, regardless of the material used to confer osteoconductive properties to the inoculum, be it a bone-derived matrix of undefined composition, or a HAP matrix exempt of proteins. It should be noted that results substantially the same as those illustrated for protein combined with hydroxylapatite alone were also generated when protein was combined with a matrix consisting of 0.5 mg hydroxylapatite, 0.5 mg gelatin and 0.5 mg collagen type I.

Figure 3A:
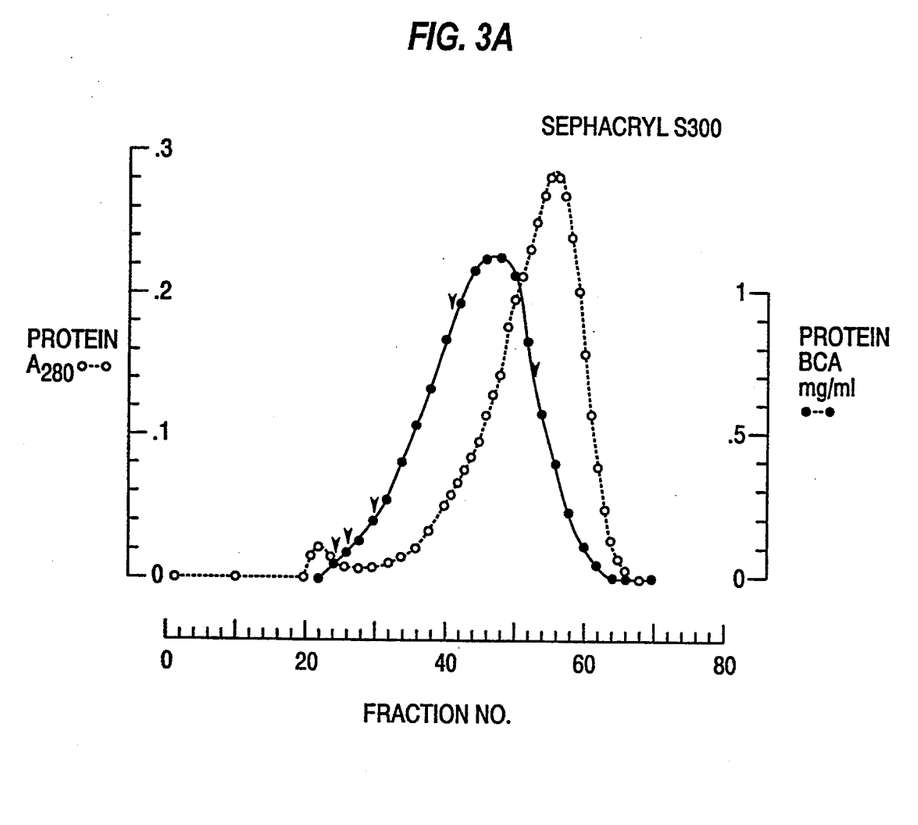
FIG. 3 illustrates the elution profile of osteogenic factor during fractionation by gel filtration on a Sephacryl S 300 column, under dissociative conditions (Gdn. HCl).
Figure 3B:
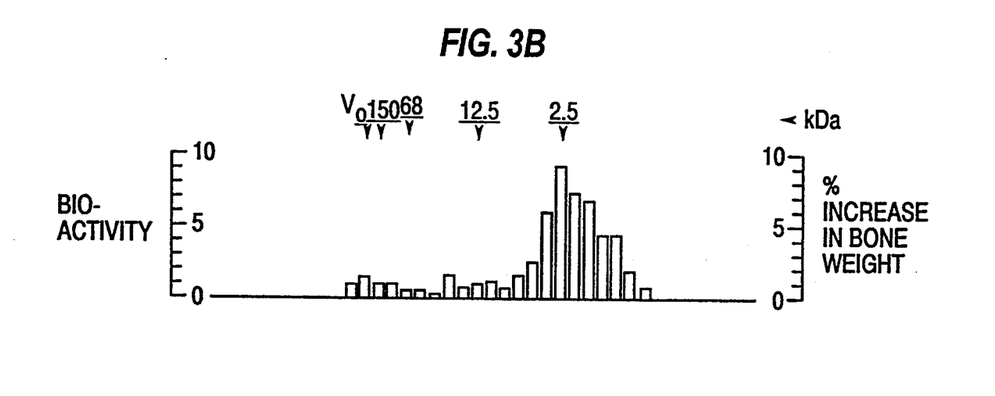

Fractionation by Gel Permeation Chromatography 170 mg of enriched bone extract were resuspended in 2 mL of a buffer solution containing 50 mM Tris-HCl (pH 7.4) and 4M of ultrapure guanidinium chloride (Gdn. HCl), incubated at 37° C. for 20 min and spun down in an Eppendorf centrifuge (at 12,000 g×5 min). The supernatant, containing about 24 mg of proteins (BCA dye method) was carefully aspirated and applied to a 1.5 cm×33 cm column packed with Sephacryl S300 superfine gel (Pharmacia Canada Inc., QB), equilibrated at room temperature in the same buffer. One mL fractions were collected at a flow rate of 12 mL per hour. The protein content of each fraction was monitored by absorbance readings at 280 nm as well as with the BCA dye method, using serum albumin dissolved in the same Tris-Gdn buffer for the calibration, as illustrated in FIG. 3. The column was calibrated with known Mr markers which elute at distinct positions that are indicated with arrows: Blue Dextran (Mr=1-2 MDa, Vo), bovine IgG immunoglobulin (Mr=150 kDa Sigma); bovine serum albumin (Mr=68 kDa) and cytochrome C (Mr=12.5 kDa) from Boehringer Mannheim Canada Ltd., Laval, QB; and bovine insulin A-chain, oxidized (Sigma). Every second fraction was dialysed at room temperature against deionized and sterile water (3×1 Liter) using Spectrapor #6 tubings (Spectrum Medical Industries, Inc., Los Angeles, Calif.), of nominal Mr=1 kDa cut-off. The protein content of each dialysed fraction was re-determined, and usually represented 5 to 10% of its original value, prior to dialysis. Each fraction was mixed with 0.5 mg HAP matrix, subjected to lyophilization, reconstituted in 0.1 ml of saline solution and injected into a single rat.

Figure 9:
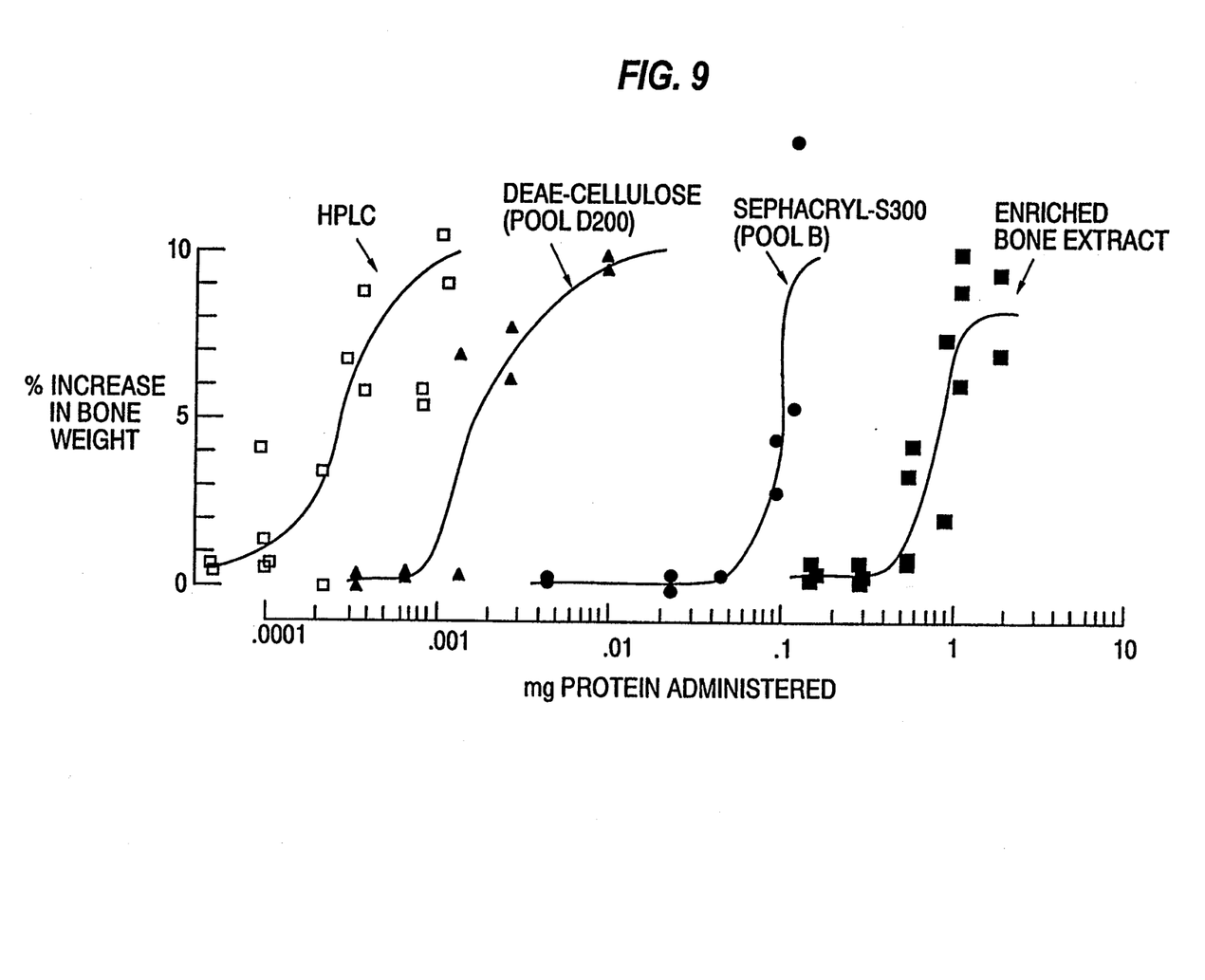
FIG. 9 illustrates the protein dose-response relationships elicited by the osteogenic factor at various stages during isolation.

The assay reveals that the osteogenic activity residing in enriched calf bone extracts is associated with molecular species migrating as a nearly symmetrical peak that coincides with the elution position of the insulin A-chain marker of Mr=2.5 kDa (see FIG. 3). On this basis, the osteogenic factor is characterized herein as having a molecular weight of "about" 2.5kDa, where the margin of error is about ±1 kDa. Bioactive fractions present in the peak (#58 to 62) contain between 30 and 55 ug of proteins, and elicit an osteogenic response of magnitude equivalent to that elicited by 250 to 500 μg of proteins of the original enriched bone extract. Accordingly, a nearly 10-fold enrichment in specific activity is estimated to be achieved following Sephacryl gel filtration and dialysis (FIG. 9).

To confirm that the bioactivity is confined to molecular species of Mr below 5 kDa, the remaining alternate fractions of the column that were not tested were subsequently pooled, dialysed, concentrated by lyophilization and bioassayed as described above. Results indicate the following % increase in bone mass: 0% for pool A (fractions # 20 to 47; 480 μg of protein injected); 6.6% for pool B (fractions # 49 to 53; 56 μg of protein); and 5.3% for pool C (fraction # 55 to 68; 6 μg of protein). For comparison, the osteogenic activity of bovine osteoinductive factor, bovine osteogenic protein-1, bone morphogenetic protein-2 and the bovine cartilage inducing factors A and B have been reported to elute from Sephacryl columns developed under similar dissociative and buffer conditions, in a Mr range from 20 to 40 kDa, and typically around 30 kDa.

Fractionation by Affinity Chromatography on Heparin-Sepharose

Figure 4A:
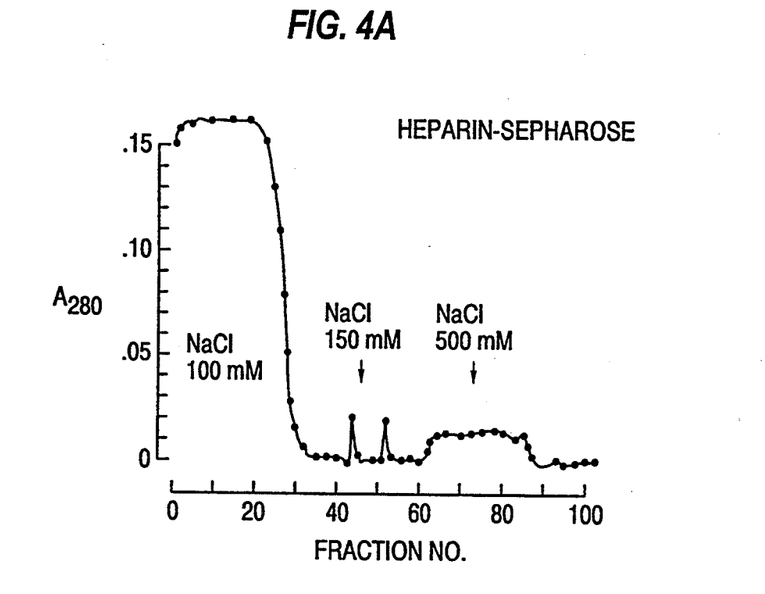
FIG. 4 illustrates the elution profile of the osteogenic factor on a Heparin-Sepharose column, under dissociative conditions (urea). Actual protein amounts (in µg) bioassayed are indicated.
Figure 4B:
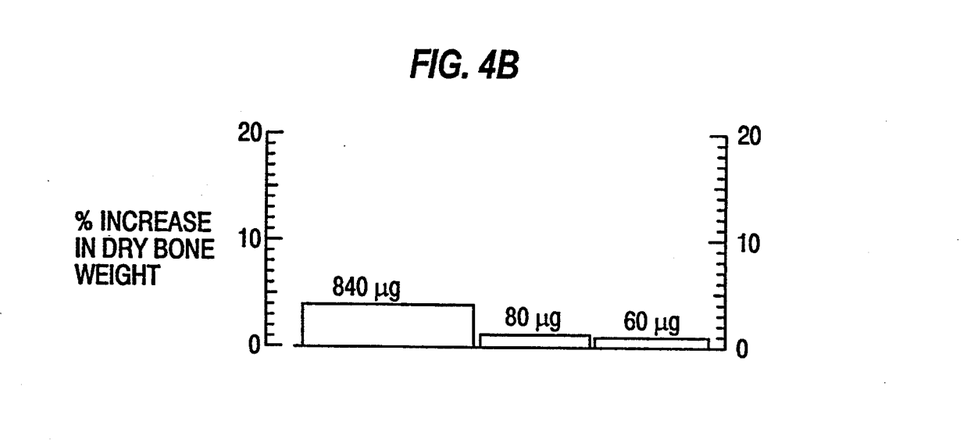

A sample was prepared similarly to the procedure detailed above, starting from 100 mg of enriched bone extract, and using a 50 mM Tris-HCl (pH 7.2), 100 mM NaCl and 6M ultrapure urea solution as an extracting buffer. The resulting supernatant of centrifugation which was estimated to contain 20 mg of proteins was adjusted to 10 mL and added to a slurry of Heparin-Sepharose CL-6B (5 g dry weight equivalents; Pharmacia) equilibrated in the same urea-containing buffer. The batchwise incubation continued overnight at room temperature after which the mixture was poured into a 1.5 cm×9 cm column. The flow through and washing fractions (1 mL) were collected until the absorbance at 280 nm decreased to less than 0.01. A stepwise elution protocol was then initiated by increasing the NaCl concentration of the 50 mM, Tris-HCL, 6M urea buffer (pH 7.2) from 100 mM to 150 mM and 500 mM, as illustrated in FIG. 4.

The three NaCl-eluted fractions were pooled separately, dialysed and lyophilized. After reconstitution in water the three pools were found to contain 98%, 1% and 1% respectively of the totally recovered proteins through the separation. Thus, the great majority of the proteins present in the enriched bone extract do not appreciably bind to heparin, and the osteogenic factor is accordingly herein characterized as having "substantially" no heparin-binding affinity. As shown in FIG. 4, only the first pool, which elutes with less than about 100 mM NaCl, elicits a significant osteogenic response when administered in the presence of a HAP matrix. Due to the lack of even modest affinity of the desired product for Heparin, no significant enrichment in specific activity is afforded by this separation method. This is in marked contrast to the situation that prevailed during the previously reported purification of osteoinductive factor, osteogenic protein-1, osteogenin and bone morphogenetic protein-2 since all these bioactive peptides characteristically bind to Heparin-Sepharose with such an affinity as to require at least 0.5M NaCl in order to be eluted.

Fractionation by Adsorption Chromatography on Hydroxyl-Apatite

Figure 5A:
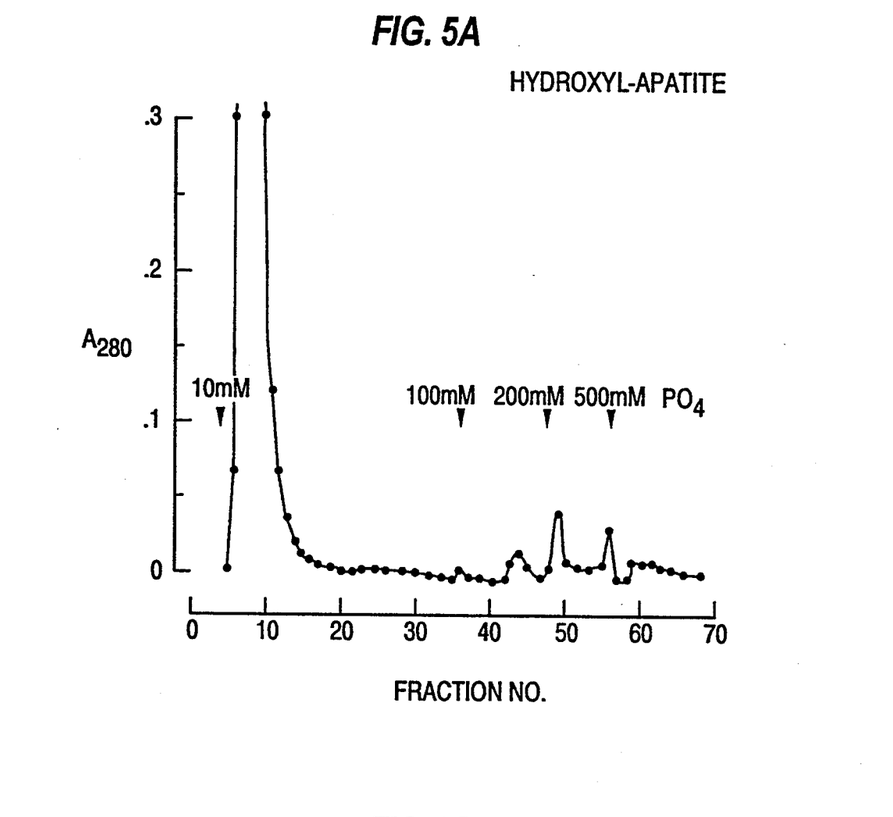
FIG. 5 illustrates the elution profile of osteogenic factor on a Hydroxyl-Apatite column, under dissociative conditions (urea). Actual protein amounts (in µg) bioassayed are indicated.
Figure 5B:
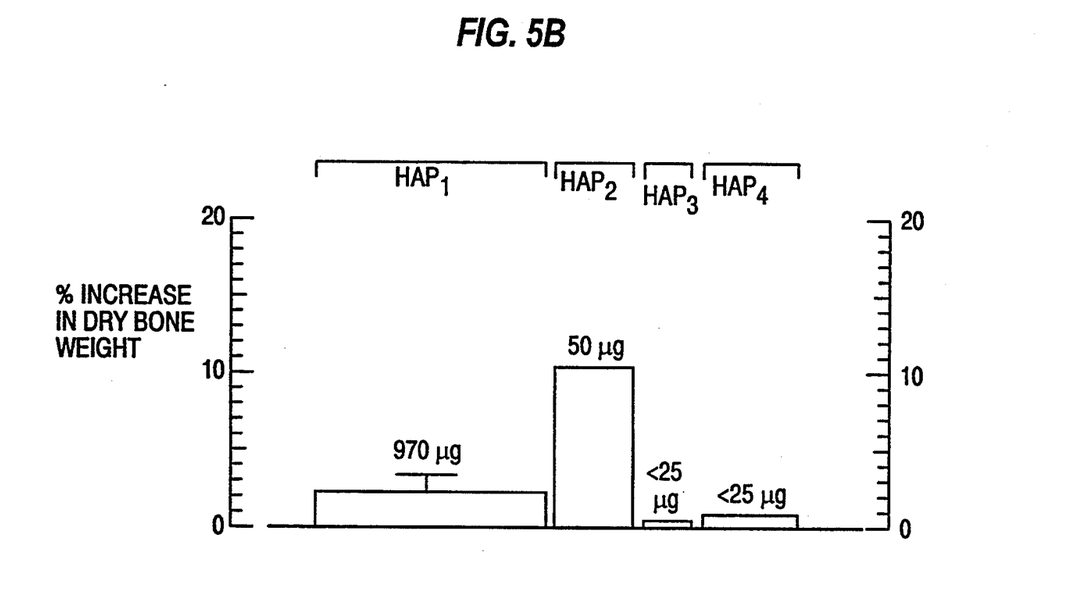

A sample was prepared similarly to the procedures detailed in section above, starting from 100 mg of enriched bone extract and using a 50 mM Tris-HCl (pH 7.0), 6M urea, 500 mM NaCl and 10 mM $Na_2HPO^4$ solution as an extracting buffer. The supernatant of centrifugation, which was estimated to contain 20 mg of proteins was applied to 1.5 cm×10 cm column packed with Hydroxyl-Apatite (Biogel HT from Bio-Rad Laboratories, Richmond, Calif.) equilibrated at room temperature in the same buffer. Fractions (1 mL) were collected until the absorbance at 280 nm decreased to baseline. Elution was initiated by increasing the $Na_2HPO_4$ concentration in the same Tris-urea containing buffer in stepwise fashion from 10 mM to 100 mM (pH 7.8), 200 mM (pH 8.0) and 500 mM (pH 8.5), as illustrated in FIG. 5.

Fractions corresponding to the four elution steps were pooled, dialysed and lyophilized. After redissolution in water, these four pools were found to contain 98.7%, 1.3% and negligible amounts of the totally recovered proteins. From the results of the bioassays (FIG. 5), it is evident that the biologically active species present in enriched bone extracts have, together with the majority of the proteins, a modest affinity for Hydroxyl-Apatite, since they are eluted completely at 100 mM $Na_2HPO_4$.

Fractionation by Ion-Exchange Chromatography

Figure 6A:
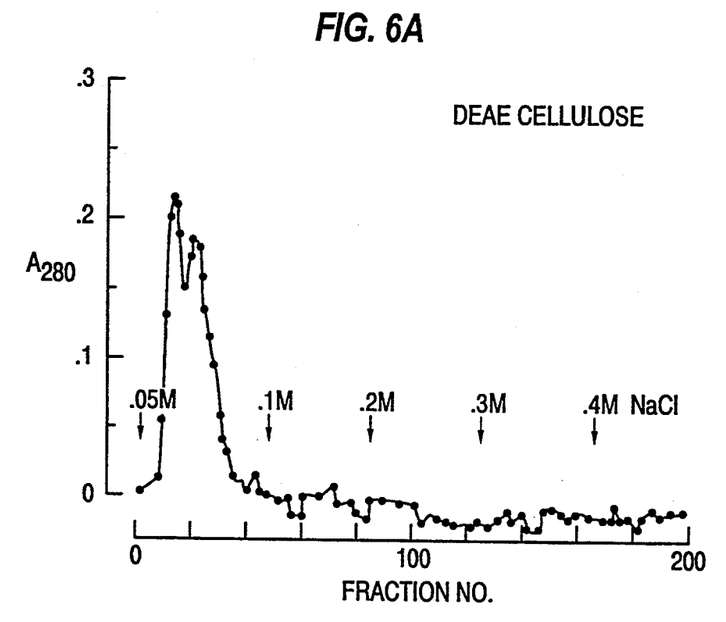
FIG. 6 illustrates the elution profile of osteogenic factor on a DEAE-cellulose column at pH 7.2 and under dissociative conditions (urea). Actual protein amounts (in µg) bioassayed are indicated.
Figure 6B:
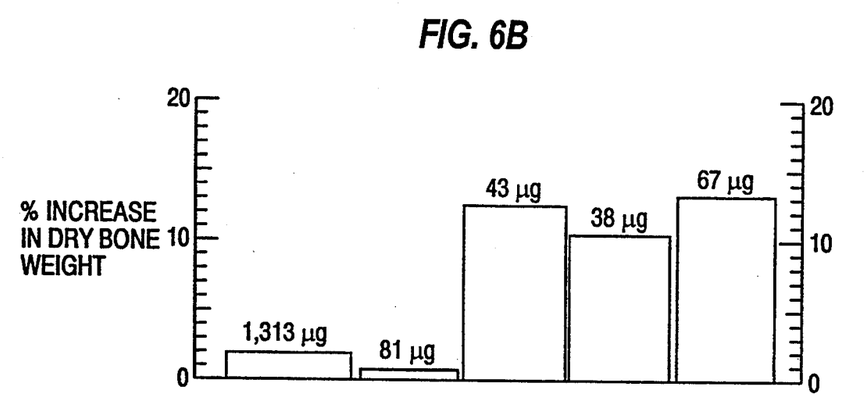

One hundred mg of enriched bone extracts were resuspended in 2 mL of a buffer solution consisting of 50 mM Tris-HCl (pH 7.2), 6M urea and 50 mM NaCl, incubated at 37° C. for 20 min and spun down. The resulting supernatant which was estimated to contain 12.4 mg of proteins was applied to a Diethyl Amino ethyl (DEAE)-Cellulose column (Whatman DE-52 microgranular from Mandel Scientific, Rockwood, ONT.; 2.5 cm×5.5 cm) equilibrated at room temperature in the same buffer. Unbound material and material washed with the same buffer were collected as 1 mL fractions until the absorbance diminished below 0.01. A stepwise elution was established using the same Tris-urea buffer as above (pH 7.2) but containing 100, 200, 300 and 400 mM NaCl respectively, as illustrated in FIG. 6.

Pooled fractions corresponding to each elution step were dialysed, lyophilized, reconstituted in water and submitted to the bioassay. Activity was recovered in the fraction eluting at $\geq 200$ mM NaCl, which contained less than 1% of the recovered proteins (FIG. 6). Based on protein amounts found to be sufficient to elicit an osteogenic response, the specific activity of DEAE-Cellulose eluted fractions is estimated to be at least 500-fold higher than that of the enriched bone extract starting material. The bioactive molecular species present in enriched bone extract can be retained on an anionic exchanger, an indication either of negative charge at pH 7.2, or of an amphoteric nature with a pI of less than 7.2. For comparison, several bone morphogenetic protein species were reported not to be retained by a DEAE-Cellulose resin.

Figure 7A:
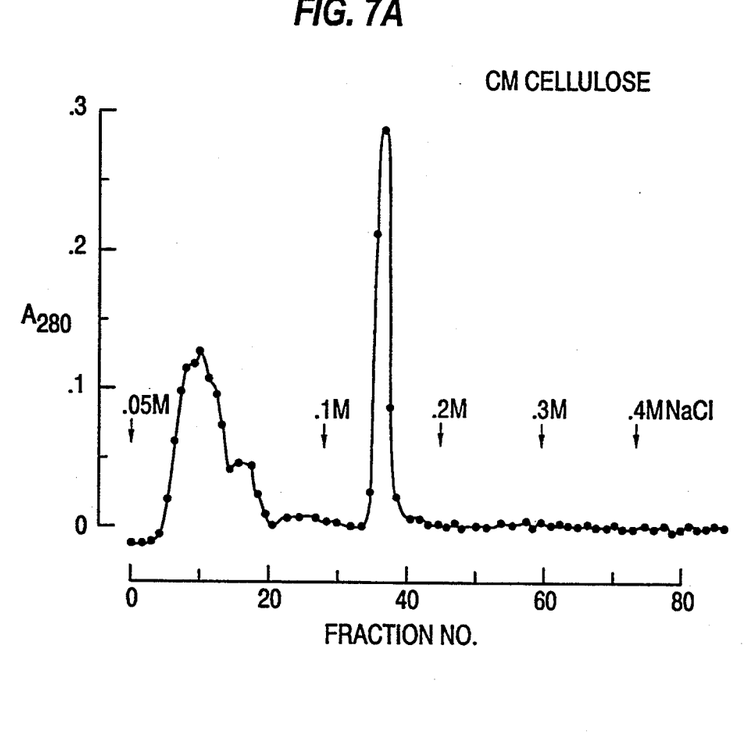
FIG. 7 illustrates the elution profile of the osteogenic factor on a CM-Cellulose at pH 4.6 and under dissociative conditions (urea). Actual protein amounts (in µg) bioassayed are indicated.
Figure 7B:
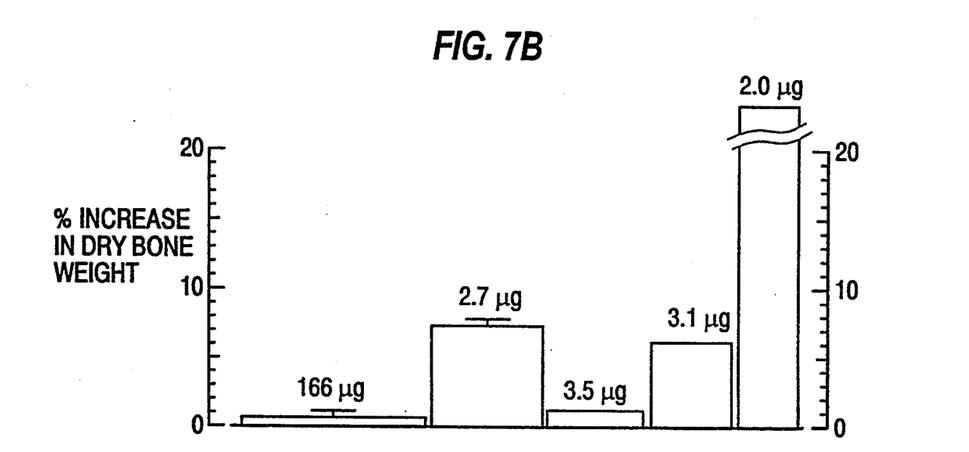
Figure 8A:
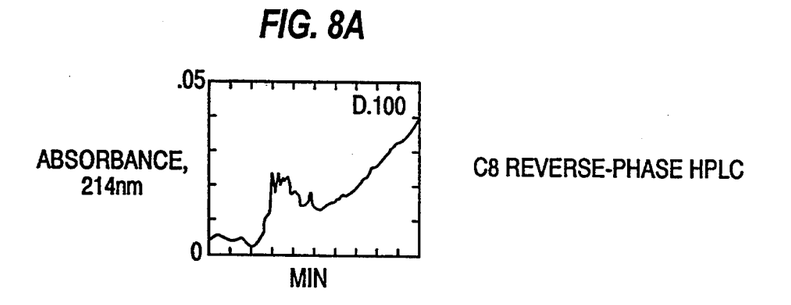
FIG. 8 illustrates the elution profile of the osteogenic factor on a C8 reversed phase HPLC column developed with a gradient of acetonitrile in 0.1% trifluoroacetic acid.
Figure 8B:
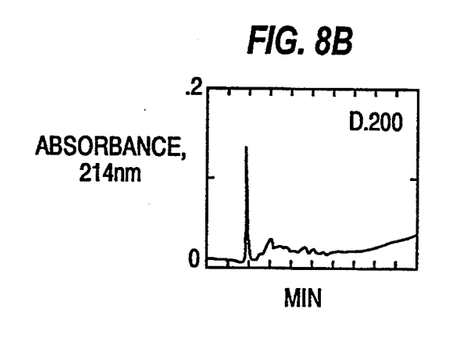
Figure 8C:
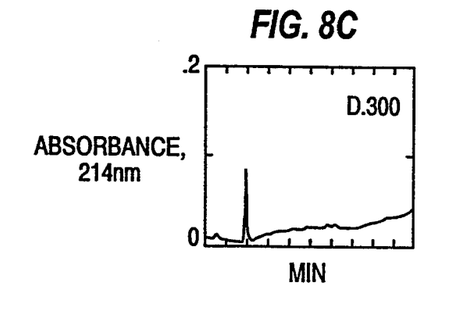
Figure 8D:
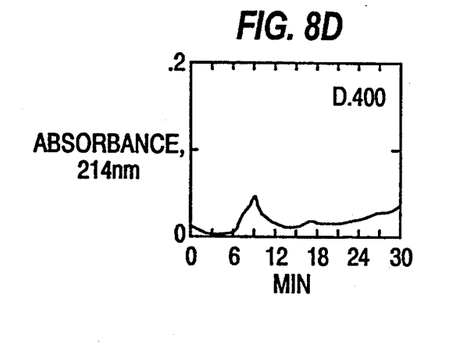
Figure 8E:
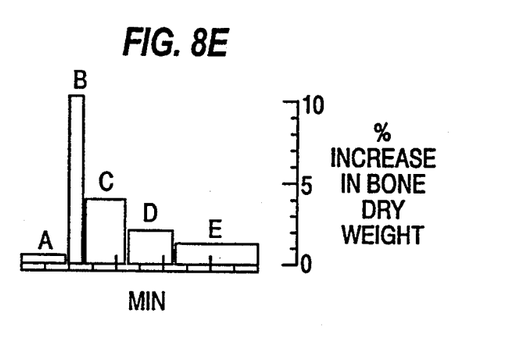
Figure 8F:
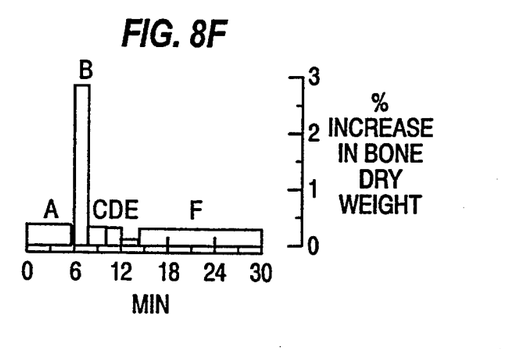

An identical procedure was adopted to separate enriched bone extracts on a Carboxyl Methyl (CM)-Cellulose column (Whatman CM-52, 2.5 cm×5.5 cm) except that 3 mL fractions were collected and that the buffer used was 50 mM Sodium acetate (pH 4.6), 6M urea and 50 mM NaCl. Results illustrated in FIG. 7 indicate that all the bioactive species were retained by the resin and variably eluted thereafter. In spite of its high absorbance at 280 nm, the 100 mM NaCl eluted pool contained only 1% of the recovered proteins after dialysis. Ninety four % of the proteins did not bind to the column. Based on protein amounts found to be sufficient to elicit an osteogenic response (2 to 3.5 µg, FIG. 7) it is estimated that a minimum 100-fold enrichment in specific activity was achieved after CM-Cellulose chromatography. Binding of the bioactive species to both anion-and cation-exchangers strongly suggests an ampholyte character equivalent to that of polypeptides and proteins having a pI ranging between 4.6 and 7.2.

Example 2: Three-Step Purification Protocol

Two hundred mg of enriched calf bone extracts were dissolved at 37 C in a buffer consisting of 50 mM Tris-HCL buffer (pH 7.2), 6M urea and 50 mM NaCl, and spun down. The supernatant, which was estimated to contain 25 to 30 mg of proteins was applied to a Sephacryl S300 gel filtration column equilibrated in the same buffer. Eluted fractions (1.1 mL) were collected as detailed above and those estimated to contain the bioactive material (i.e. fractions #45 to #71) were pooled (~30 mL total volume) and then directly applied to a DEAE-Cellulose column equilibrated in the same buffer. A stepwise elution procedure identical to that detailed above was then applied, leading to pools D50 to D400 respectively.

Each pool was dialysed against water, lyophilized and reconstituted in 2 mL of deionized water. Aliquots were bioassayed to confirm the presence of osteogenic activity in pools D200, D300, and to a lower extent in D400. Another aliquot of each DEAE-Cellulose pool D50 to D400, corresponding to approximately 3 µg of protein, was acidified to pH 4.0 by the addition of 0.1% trifluoroacetic acid (TFA) and loaded separately on a C8 reverse phase column (2.1×30 mm Aquapore RP-300 narrowbore, 300 A pore size, from Applied Biosystems Canada Inc., Mississauga, ON.). Ten percent of the eluting solvent (80% acetonitrile, 20% water, 0.1% TFA) was applied at room temperature for 2 minutes followed by a 10 to 70% linear gradient (from 2 to 26 min), followed by a 70 to 100% gradient (26 min to 30 min), the flow rate being maintained constant at 0.1 mL per min. The absorbance at 214 nm which is characteristic of peptide bonds was recorded, and is shown in FIG. 8.

As shown in FIG. 8, pooled fractions D100 to D400, eluted from the DEAE-Cellulose column, contained unresolved material that appeared as a cluster of overlapping absorbance peaks in the 7 to 20 min region of the reverse phase-HPLC separation. However, only pooled fractions D200 and D300, which comprise the osteogenic factor, were characterized by the presence of an additional absorbance peak, with an earlier retention time of 6 0.5 min, that eluted at between 15 and 20% acetonitrile. The protein content of this unique peak was estimated to account for 8 2% of the eluted material. Several samples of the D200 pool, amounting to 43 µg of protein, were then applied to the C8 reverse phase-HPLC column under identical conditions and 5 fractions were collected: A (0 to 6 min), B (6 to 7 min), C (7 to 13 min), D (13 to 19 min), E (19 to 30 min). After lyophilization and reconstitution, fractions were bioassayed in duplicate. Similarly, 17 ug of protein from the D300 pool were processed and 6 fractions were collected and bioassayed.

FIG. 8 reveals that the osteogenic activity was found in fraction B which coincides with the well individualized absorbance peak identified above at 6 min retention time. An estimated amount of less than 1 μg of such reverse-phase HPLC purified material is sufficient to elicit a biological response under the conditions of the assay.

Other characteristics of the osteogenic factor have also been assessed, and the results of these assessments are provided below.

Effect of Reducing Agents

A common feature shared by virtually all multimeric osteogenic factors is loss of activity following reduction. When enriched calf bone extracts (5.85 mg of protein) were incubated for 2 hours at 37 C in a 50 mM Tris-HCl buffer (pH 7.4) containing 4M Gdn.HCl and either 10 mM 2-mercaptoethanol (ME) or 10 mM dithiothreitol (DTT), dialyzed extensively against pure water at room temperature, then lyophilized and reconstituted with a HAP matrix, they were found to retain their osteogenic potential. Therefore, reduction of putative disulfide bonds seems not impair the function of the present osteogenic factor.

Testing for Competence in a Mitogenic Assay

Evidence indicating that enriched calf bone extracts are completely devoid of classical mitogenic potential in vitro on either rodent osteoblasts or fibroblasts is presented below, using tissue culture techniques and bioassays known in the art.

Three types of cells were investigated: rat kidney NRK-49F fibroblasts; Chinese hamster lung CCL39 fibroblasts; and an osteoblast-enriched, alkaline phosphatase-positive cell suspension obtained by sequential digestion with collagenase and dispase (Boehringer) of new born rat calvaria, as described by Wong, G. L. & Cohn, A. V. (1975) Proc. Natl. Acad. Sci. USA, 72:3167–3171. Approximately $2 \times 10^5$ cells were inoculated in 24-well tissue culture plates, in duplicate, in HAMF12: DMEM medium (Gibco) containing 10% heat-inactivated fetal calf serum (Gibco). One day later, the medium was replaced with serum-free medium to induce quiescence. Growth-promoting agents or test substances were then added together with 1 μCi of [$^3$H]-methyl thymidine (Amersham) in a 500 μl volume. Forty-eight hours later the medium was aspirated and the monolayer was extracted to measure trichloroacetic acid-precipitable (i.e. DNA) radioactivity in a liquid scintillation counter. Test substances included various concentrations of fetal calf serum (FCS), mouse epidermal growth factor, bovine α-thrombin, and an aqueous solution of enriched calf bone extract. The latter was prepared by centrifuging a 10 mg/ml suspension made in the serum-free medium described above and filter-sterilizing (Milipore 0.22 μm) the resulting supernatant.

Figure 10A:
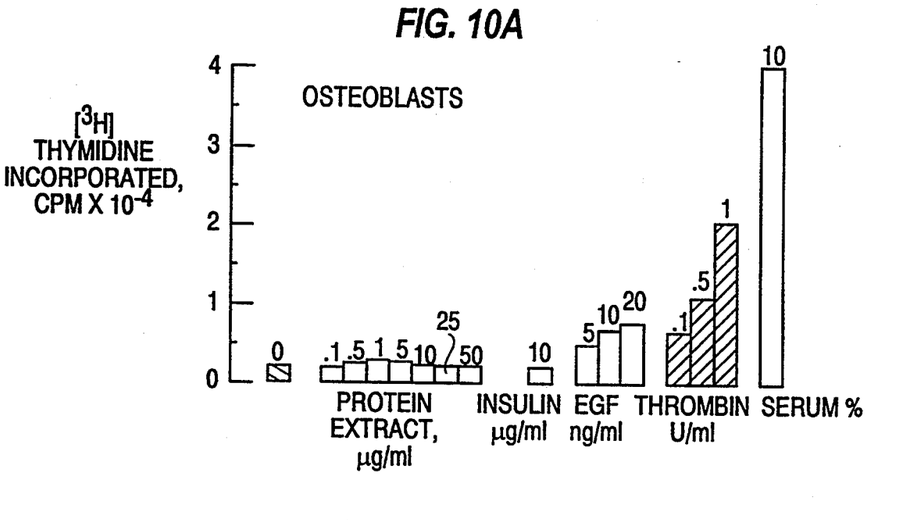
FIG. 10 illustrates the mitogenic effect elicited by the osteogenic factor, insulin, epidermal growth factor, a-thrombin and serum toward rat osteoclasts, and fibroblasts of the CCL39 and NRK-49F lineages.
Figure 10B:
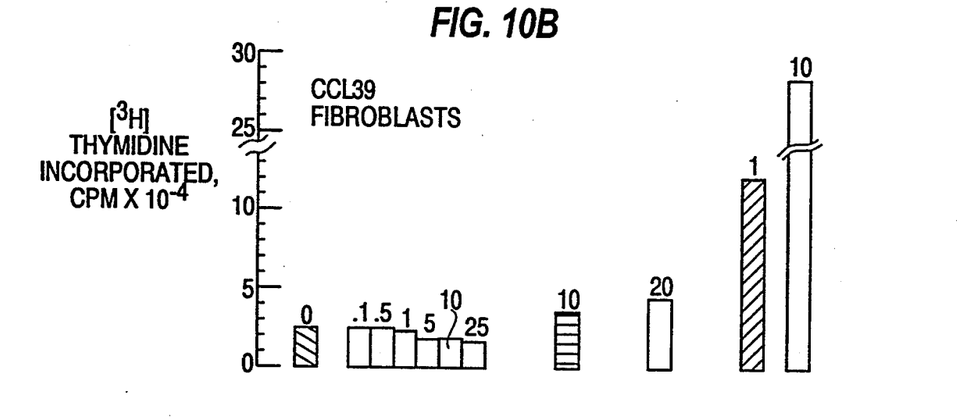
Figure 10C:
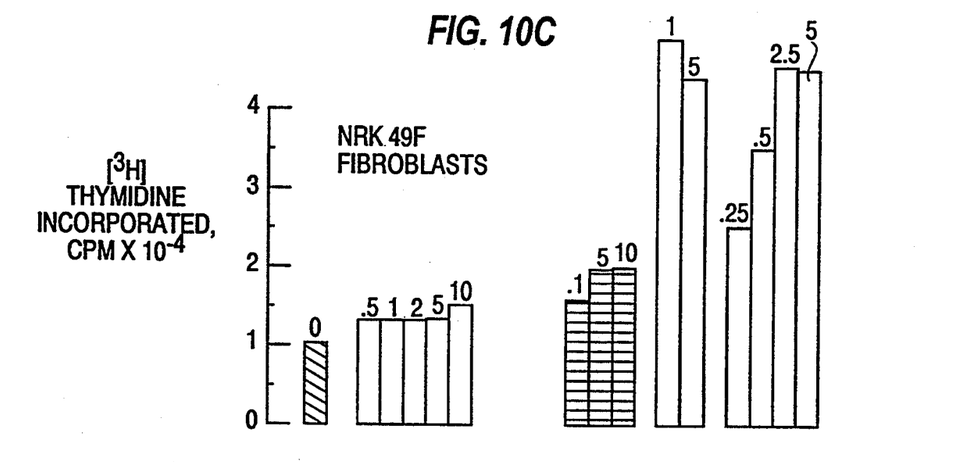

Results illustrated in FIG. 10 indicate that concentrations of enriched bone extracts up to 40 μg/ml protein are unable in vitro to re-initiate DNA replication in quiescent calvarial osteoblasts, CCL39 or NRK-49F fibroblasts, unlike recognized mitogenic substances such as serum, purified EGF or α-thrombin. Since the same three cell types have been reported to respond also to basic and acidic FGF and PDGF under identical conditions, it is reasonable to conclude that no substantial amounts of any of these growth factors are present in the enriched calf bone extracts from which the present osteogenic factor was isolated. Presumably, many such growth factors that are known to be present in bovine bones and that can be released during the demineralization step were destroyed by pepsin treatment.

We claim:

1. A method for obtaining a water-soluble osteogenic factor capable of inducing bone formation in a mammal, comprising the steps of obtaining a mammalian bone extract containing the factor, treating the bone extract with water to obtain an aqueous extract containing said factor, treating said aqueous extract with alcohol to form a precipitate containing said factor, treating said precipitate with water to obtain an aqueous solution that contains said factor, and then fractionating said aqueous extract to recover therefrom an osteogenic factor having a molecular weight of about 2.5kD when measured by gel filtration under dissociating condition, having an isoelectric point in the pH range of 4.6 to 7.2, and having a specific activity of at least about 10 units/mg in the rat bone growth assay.

2. The method according to claim 1, wherein said mammalian bone extract is an extract of bovine bone.

3. The method according to claim 2, wherein said aqueous extract is size-fractionated under dissociating conditions to recover material having a molecular weight of about 2.5 kD.

4. The method according to claim 2, wherein said aqueous extract is fractionated by ion exchange chromatography to recover material having a pI in the range from 4.6 to 7.2.

5. The method according to claim 4, wherein the material recovered following fractionation by ion exchange chromatography is subsequently subjected to reversed phase high performance liquid chromatography, and material having a specific activity in the rat bone growth assay of at least about 3,000 units/mg is recovered.

* * * * *